United States Patent [19]

Lissot et al.

[11] Patent Number: 4,471,677
[45] Date of Patent: Sep. 18, 1984

[54] DEVICE FOR PRODUCING CYLINDRICAL CAVITIES IN A LAYER OF GELLED MATERIAL

[75] Inventors: Jean Lissot, Brie-Comte-Robert; Claude Pascal, Combs La Ville, both of France

[73] Assignee: Rhone-Poulenc S.A., Courbevoie, France

[21] Appl. No.: 465,019

[22] Filed: Feb. 8, 1983

[30] Foreign Application Priority Data

Feb. 9, 1982 [FR] France ............................. 82 02057

[51] Int. Cl.³ .......................... B26F 1/38; B26F 3/08
[52] U.S. Cl. ...................................... 83/100; 83/171; 83/618; 83/632; 83/684
[58] Field of Search ................ 83/100, 171, 618, 632, 83/684, 925 R

[56] References Cited

U.S. PATENT DOCUMENTS

| | | | |
|---|---|---|---|
| 2,463,455 | 3/1949 | Dann | 83/100 X |
| 3,248,980 | 5/1966 | Downing | 83/100 X |
| 3,863,533 | 2/1975 | Hurn | 83/100 |
| 4,012,275 | 3/1977 | Sjöholm et al. | 83/100 X |

Primary Examiner—Frank T. Yost
Attorney, Agent, or Firm—Stevens, Davis, Miller & Mosher

[57] ABSTRACT

Semi-automatic device which makes it possible to produce cylindrical cavities, according to a given geometrical arrangement, in a layer of gelled material, the said device consisting of a set of several individual devices each of which, as shown in FIG. 1, consists of a cutter inside which a suction tube slides, it being possible for a pressure reduction to be created in the said suction tube.

5 Claims, 3 Drawing Figures

DEVICE FOR PRODUCING CYLINDRICAL CAVITIES IN A LAYER OF GELLED MATERIAL

DESCRIPTION

The present invention relates to a device which makes it possible to produce cylindrical cavities in a layer of gelled material.

An antibiotic possesses an inhibitory action against living microorganisms, and this property can be utilised for its detection and determination during the various stages of its manufacture.

The methods conventionally used for microbiological determinations include the diffusion method, which consists in placing series of solutions of the antibiotic whose concentrations are in a given common ratio, generally 1.5 or 2, on the surface of plates carrying inoculated agar medium, generally in Petri dishes. After incubation, circular inhibition zones appear, the diameter of which bears a linear relationship to the logarithm of the concentrations. The determination is carried out by comparing the results obtained for the sample with those obtained for a standard.

Because of the random nature of biological results, a microbiological determination must be repeated. To allow for certain uncontrollable modifying factors, it is necessary to adopt experimental procedures which enable them to be taken into consideration. Thus, to carry out a single determination, it is customary to use 10 to 20 Petri dishes, corresponding to 30 to 60 results, for the standard. Furthermore, for the same reasons, a determination must be repeated several days in succession in order to obtain the desired precision.

It is particularly important to be able to automate the method as much as possible, in view of the large number of determinations which must be recorded. Furthermore, automation permits a considerable reduction in the risks of errors.

To carry out the diffusion method, it is necessary to produce cylindrical cavities in the inoculated nutrient medium for the purpose of receiving the antibiotic solutions, which cavities must be identical, have smooth walls and not contain particles of residual materials. The agar is a gelled material of variable consistency and weak cohesion, thus posing some problems in cutting out the cavities accurately. Moreover, when these cavities are cut out, it is particularly important not to detach the gelled material, such as the agar, from the bottom of the vessel which contains it. In this way, it is possible to obtain uniform diffusion of the antibiotic through the gelled material, which permits a clear limitation of the inhibition zone.

According to the present invention we provide a device for producing cylindrical cavities in a layer of gelled material, said device comprising:

(a) a plurality of tubular cutters;

(b) an internal chamfer on the lower end of each cutter defining a very sharp annular cutting edge at said lower end;

(c) means for positioning a dish of gelled material below said cutters;

(d) means for raising and lowering the cutters together between a raised position and a lowered position in which the cutting edges are in contact with the bottom inner surface of a dish so positioned;

(e) a suction tube mounted co-axially within each tubular cutter;

(f) a notched bottom end to each suction tube;

(g) means for raising and lowering the suction tubes together between a raised first position and a lowered second position in which the notched bottom end is adjacent the bottom inner surface of a dish so positioned;

(h) a suction chamber;

(i) pipes connecting said suction chamber to each suction tube;

(j) means for selectively applying suction to said suction chamber; and (k) synchronizing means controlling the operation of said device such that the means for raising and lowering the cutters and the suction tubes are operated, whereby (i) the cutters are caused to enter perpendicular to the surface of the gelled material until they come into contact with the inner surface of the bottom of the dish;

(ii) suction is applied to said suction chamber and thus via said pipes to said suction tubes, which are lowered into the gelled material until they reach their second lowered position;

(iii) the suction tubes are raised and atmospheric pressure is re-established;

(iiii) the cutters are raised.

It is thus possible for cavities having the required characteristics to be produced simultaneously by means of a semi-automatic device, which also permits a symmetrical distribution of these cavities over the surface of the gelled material.

In order that the present invention may more readily be understood, the following description is given, merely by way of example, reference being made to the accompanying drawings, in which.

Figure 1:
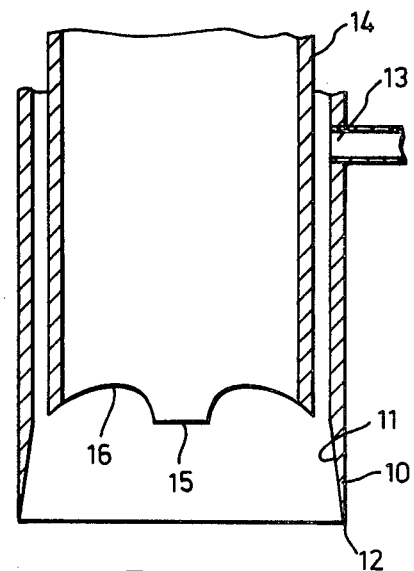
FIG. 1 is a schematic cross-section through one embodiment of cutter and suction tube of a device according to the present invention.

Referring first to FIG. 1 there is illustrated very schematically a tubular cutter 10 having an internal chamfer at 11 and defining a very sharp cutting edge 12 of negligible width. At least one port 13 is formed in the tubular cutter 10 and enables the cutter to be vented to atmosphere.

Mounted co-axially within the cutter 10 is a suction tube 14 the lower edge 15 of which is provided with a plurality of circumferentially spaced notches 16.

Figure 3:
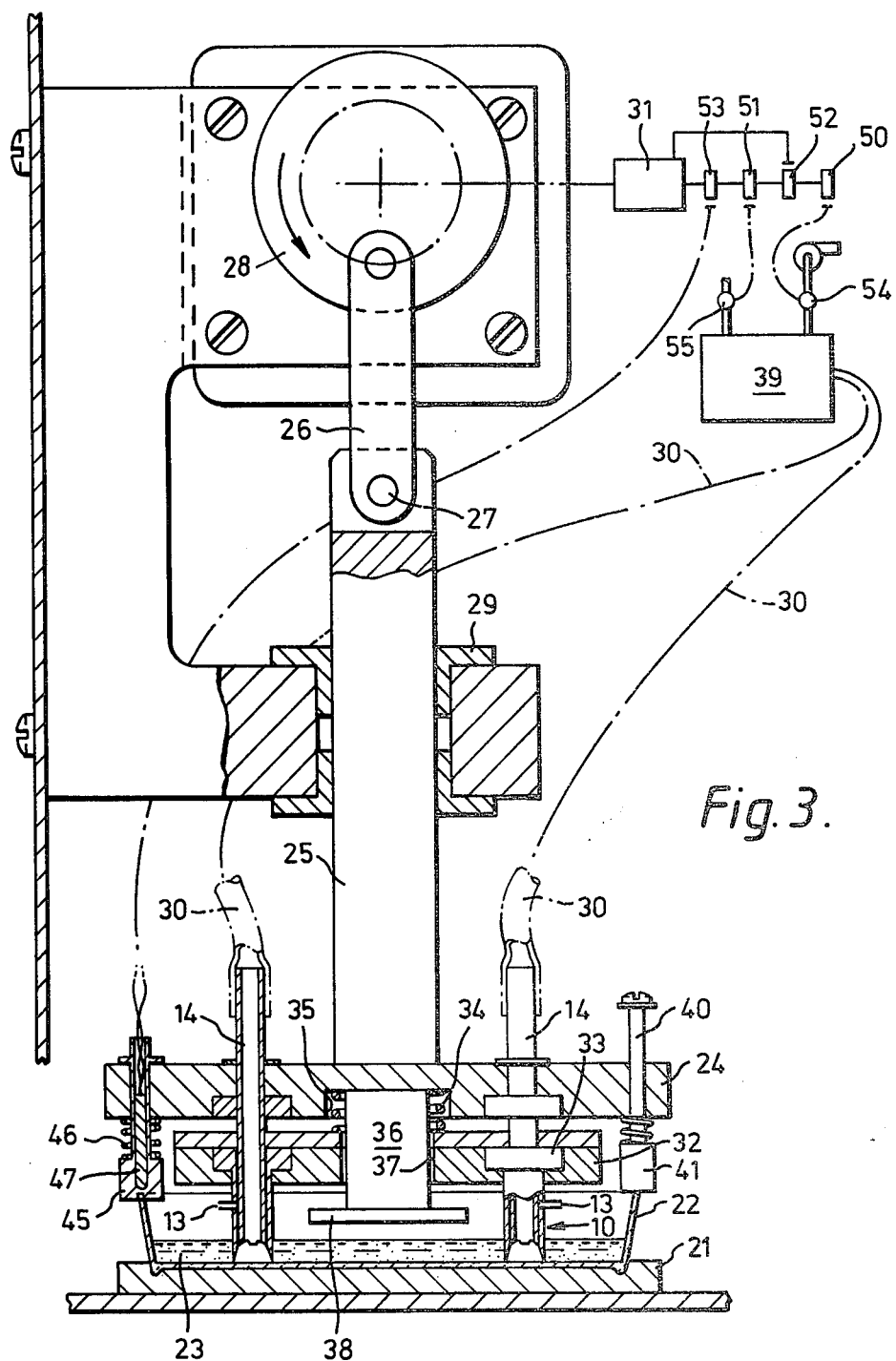
FIG. 3 is a side elevation, partly in cross-section of one embodiment of device according to the present invention.

FIG. 3 shows, to a reduced scale, a device according to the present invention incorporating several cutter/suction tube assemblies, 10, 14 as shown in FIG. 1. The device includes a table 20 provided with a support slide 21 for a Petri dish 22 of conventional design. The slide 22 can be moved between a fixed operating position as shown and an out-of-the-way position at which the Petri dish can be removed. The Petri dishes are shown with a quantity 23 of agar therein.

A support plate 24 is mounted on a vertically extending central shaft 25 which is connected via a rod 26 journaled thereto at 27 with a crank wheel 28 which can be driven by a variable speed DC electric motor shown schematically at 31. The shaft 25 is mounted in a sliding bearing 29 enabling it to execute a vertical reciprocatory motion as the result of the action of the crank wheel and crank 28, 26.

Secured on the plate 24 are several suction tubes at 14 each provided with a flexible pipe 30 are connected to a common suction chamber (39). The lower ends of the suction tubes 14 have the form illustrated in the FIG. 1.

A lower plate 32 is mounted below the plate 24 and has associated therewith an axial sliding bearing 33 for each suction tube 14. The plate 32 is urged downwardly by means of a spring 34 engaged in a recess 35 in the lower surface of the plate 24. The plate 32 carries a number of tubular cutters 10, of a form as illustrated in FIG. 1, so as to surround each of the suction tubes 14. As indicated above the lower edge of the tubular cutters 10 is sharpened.

Lower portion 36 of shaft 25 is of a reduced diameter so that it can pass through a central aperture 37 in the lower plate 32 and carries, at the bottom, a foot plate 38 of larger diameter than the opening 37.

The plate 24 also carries a number of locating studs 40 each having a foot 41 engageable with the rim of the Petri dish 22 and urged downwardly by means of a spring 42. These studs 40 are circumferentially spaced around the plate 24.

At one circumferential location there is provided a blade 45, which is also spring urged down by a spring 46, and is heated by a heater probe 47.

In use of the above device, a suitable agar 23 is placed in a Petri dish 22 and the latter is introduced to the position shown on the slide 21. The motor 31 is started and causes the crank wheel 28 to rotate, this bringing about a sinusoidal reciprocatory motion of the shaft 25 and thus of the plate 24. The assembly in fact starts at a position 180° from that shown and the cutters 10 descend initially very fast due to the sinusoidal motion, and progressively more slowly until they cut through the agar and abut the base of the Petri dish. The downward movement of the shaft 25 continues and the spring 34 allows a certain lost motion to take place, during which the suction tube 14 descends through the agar to a location slightly spaced from the bottom of the Petri dish. Thereafter the suction tube begins to rise first and as the shaft 25 continues to ascend the foot 38 engages the lower surface of the plate 32 thus pulling the cutters 10 out of the agar.

Figure 2:
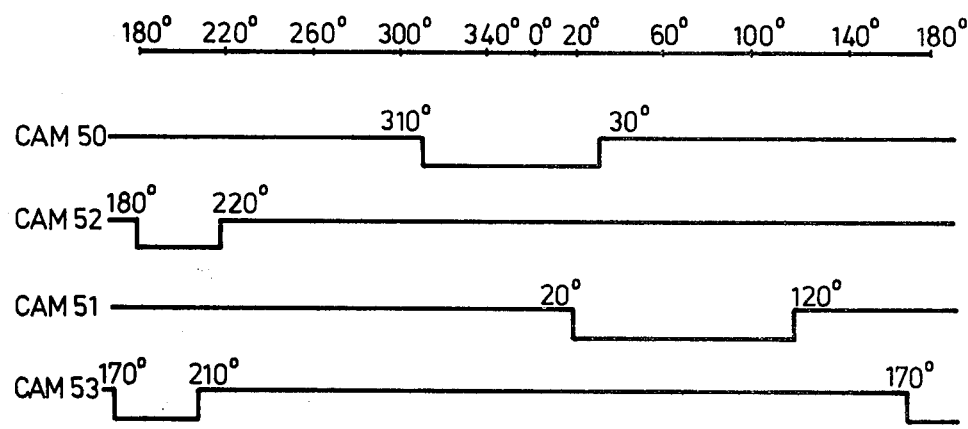
FIG. 2 is a cam lift diagram of the device.

During this operation cams 50 and 51, driven by motor 31, effect a cycle of operations on valves 54 and 55 connected to the common suction chamber 39 to which the pipes 30 are themselves connected. The cycle of operations is indicated in FIG. 2. The arrangement is such that bottom dead centre corresponds to the position 0° and the cutters 10 are actually in contact with the bottom of the dish from 300° to 60°, that is over 120° movement. The valve 54 intended to apply vacuum to the suction chamber is operated by cam 50 to provide this connection from a period of 310° to 30°, so that suction is applied for 80° of rotation. Just before the suction tube 14 comes into contact with the agar, the pressure reduction is created inside the suction tube, atmospheric pressure being maintained between the two tubes via the ports 13 provided in the wall of a cutter. Because of the reduced pressure existing in the suction tube, the gelled agar material is sucked out as the suction tube descends, and it is carried away to the common chamber 39. Under these conditions, the whole disk of gelled material is sucked out without leaving any solid particles. When the suction tube rises, and before the cutter leaves the bottom of the Petri dish containing the gelled agar material, atmospheric pressure is reestablished in the suction tube by operation of cam 51 and thus valve 55 which produces atmospheric pressure from the position 20° to the position 120°.

It is thus possible simultaneously to produce identical cavities distributed symmetrically relative to the centre of the Petri dish containing the gelled material.

As the cavities are produced simultaneously, the suction tubes are connected in parallel to the common chamber 39 for collecting the gelled material sucked out. The flexible pipes 30 serve not only to suck the gelled material out, but they form a necessary throttling function for limiting the flow of air sucked through the suction tubes 14 when all the gelled material has been carried away, so as to prevent an excessive pressure reduction from being created at the bottom of the cavity and to prevent the reduced pressure prevailing inside the common suction chamber 39 from being let down too suddenly when the gelled material is only left remaining in one or only a few of the tubes 30.

If the Petri dish is round, as is normal, then in order to distinguish between the various cavities which have been carried out, the blade 45 is heated at an appropriate time so that when the blade is pressed by the spring 46 downwardly, it forms a notch, which is preferably V-shaped, in the rim of the Petri dish. This notch can be used to identify the individual cavities formed in the agar material.

Cam 52 is used to stop the motor after each revolution at a point when the crank wheel 28 has reached its top dead centre position. The cam 53 is used to switch off the heated probe 47 to reduce the danger of the operator burning himself when the slide is moved out to replace the Petri dish. When the Petri dish is in fact pushed back to the position illustrated, a stop positioned exactly relative to the cutting and suction device as a whole automatically starts up the cycle of operations again.

We claim:

1. A device for producing cylindrical cavities in a layer of gelled material, said device comprising:
    (a) a plurality of tubular cutters;
    (b) an internal chamfer on the lower end of each cutter defining a very sharp annular cutting edge at said lower end;
    (c) means for positioning a dish of gelled material below said cutters;
    (d) means for raising and lowering the cutters together between a raised position and a lowered position in which the cutting edges are in contact with the bottom inner surface of a dish so positioned;
    (e) a suction tube mounted co-axially within each tubular cutter;
    (f) a notched bottom end to each suction tube;
    (g) means for raising and lowering the suction tubes together between a raised first position and a lowered second position in which the notched bottom end is adjacent the bottom inner surface of a dish so positioned;
    (h) a suction chamber;
    (i) pipes connecting said suction chamber to each suction tube;
    (j) means for selectively applying suction to said suction chamber; and
    (k) synchronising means controlling the operation of said device such that the means for raising and lowering the cutters and the suction tubes are operated, whereby
        (i) the cutters are caused to enter perpendicular to the surface of the gelled material until they come into contact with the inner surface of the bottom of the dish;

(ii) suction is applied to said suction chamber and thus via said pipes to said suction tubes, which are lowered into the gelled material until they reach their second lowered position;

(iii) the suction tubes are raised and atmospheric pressure is re-established;

(iiii) the cutters are raised.

2. A device according to claim 1 and further comprising a vertically reciprocable shaft, a first support plate mounted on said shaft, said suction tubes being mounted on said first support plate, a second support plate mounted below said first support plate and capable of limited relative movement with respect thereto, said tubular cutters being mounted on said second support plate whereby they are capable of limited relative movement with respect to the suction tubes.

3. A device according to claim 2 and further comprising a crank and connecting rod connected to said shaft and an electric motor operatively connected to drive said crank to effect reciprocation of said shaft.

4. A device according to claim 3 wherein the means for selectively applying suction to said suction chamber include two cam operated electro-valves.

5. A device according to claim 1 and further comprising a heated probe with means to raise and lower said probe so that it comes into contact with the rim of a dish on said positioning means to mark said rim.

* * * * *